(12) United States Patent
Norris

(10) Patent No.: US 9,486,349 B2
(45) Date of Patent: Nov. 8, 2016

(54) SYSTEMS AND METHODS OF DEPLOYMENT OF ENDOLUMINAL DEVICES

(71) Applicant: W. L. Gore & Associates, Inc., Newark, DE (US)

(72) Inventor: Patrick M. Norris, Bellemont, AZ (US)

(73) Assignee: W. L. GORE & ASSOCIATES, INC., Newark, DE (US)

( * ) Notice: Subject to any disclaimer, the term of this patent is extended or adjusted under 35 U.S.C. 154(b) by 289 days.

(21) Appl. No.: 13/959,540

(22) Filed: Aug. 5, 2013

(65) Prior Publication Data

US 2014/0142681 A1 May 22, 2014

Related U.S. Application Data

(60) Provisional application No. 61/682,136, filed on Aug. 10, 2012.

(51) Int. Cl.
| | | |
|---|---|---|
| *A61F 2/06* | (2013.01) | |
| *A61F 2/966* | (2013.01) | |
| *A61F 2/97* | (2013.01) | |
| *A61F 2/07* | (2013.01) | |

(52) U.S. Cl.
CPC ................ *A61F 2/966* (2013.01); *A61F 2/97* (2013.01); *A61F 2/07* (2013.01)

(58) Field of Classification Search
CPC ............ A61F 2/07; A61F 2/97; A61F 2/966; A61F 2002/075; A61F 2/95; A61M 2025/0681
USPC ........................ 623/1.11, 1.12; 606/108, 200
See application file for complete search history.

(56) References Cited

U.S. PATENT DOCUMENTS

| | | | | |
|---|---|---|---|---|
| 4,502,159 | A | * | 3/1985 | Woodroof et al. .......... 623/1.41 |
| 6,254,628 | B1 | * | 7/2001 | Wallace et al. .............. 623/1.12 |
| 6,352,561 | B1 | | 3/2002 | Leopold et al. |
| 8,236,040 | B2 | | 8/2012 | Mayberry et al. |
| 8,435,279 | B2 | | 5/2013 | Beyerlein et al. |
| 2004/0143315 | A1 | | 7/2004 | Bruun et al. |
| 2006/0047297 | A1 | * | 3/2006 | Case ......................... A61F 2/01 606/194 |
| 2009/0192518 | A1 | * | 7/2009 | Golden ..................... A61F 2/95 606/108 |
| 2011/0257720 | A1 | | 10/2011 | Peterson et al. |
| 2012/0130469 | A1 | | 5/2012 | Cragg et al. |
| 2012/0130474 | A1 | * | 5/2012 | Buckley ...................... 623/1.12 |

(Continued)

FOREIGN PATENT DOCUMENTS

WO      2012/068046      5/2012

OTHER PUBLICATIONS

International Search Report for PCT/US2013/ mailed Nov. 14, 2013, corresponding to U.S. Appl. No. 13/959,540, 6 pages.

*Primary Examiner* — Todd E Manahan
*Assistant Examiner* — Majid Jamialahmadi

(57) ABSTRACT

A removable sleeve extends around an expandable stent graft to constrain the expandable stent graft toward a collapsed configuration. The sleeve is held together by a coupling member to constrain the expandable device toward the collapsed configuration for endoluminal delivery to a vascular treatment site. The sleeve is openable by displacing the coupling member away from the sleeve to allow outward expansion of the expandable device toward an expanded configuration. The sleeve is separate from the expandable device so as to be removable from the treatment site after deployment of the expandable device.

14 Claims, 3 Drawing Sheets

(56) References Cited

U.S. PATENT DOCUMENTS

2013/0013047 A1 1/2013 Ramos et al.
2013/0103135 A1 4/2013 Vinluan
2013/0110223 A1 5/2013 Munsinger et al.
2013/0123896 A1* 5/2013 Bloss .................. A61F 2/97
 623/1.11
2014/0188210 A1* 7/2014 Beard et al. .............. 623/1.12

* cited by examiner

SYSTEMS AND METHODS OF DEPLOYMENT OF ENDOLUMINAL DEVICES

CROSS-REFERENCE TO RELATED APPLICATIONS

This application claims priority to U.S. Provisional Application No. 61/682,136, entitled "SYSTEMS AND METHODS OF DEPLOYMENT OF ENDOLUMINAL DEVICES" filed on Aug. 10, 2012, which is hereby incorporated by reference in its entirety.

FIELD

The invention relates to endoluminal devices and, more particularly, to systems and methods of deployment of endoluminal devices.

DISCUSSION OF THE RELATED ART

Endoluminal therapies typically involve the insertion of a delivery catheter to transport an implantable prosthetic device into the vasculature through a small, often percutaneous, access site in a remote vessel. Once access to the vasculature is achieved, the delivery catheter is used to mediate endoluminal delivery and subsequent deployment of the device via one of several techniques. In this fashion, the device can be remotely implanted to achieve a therapeutic outcome. In contrast to conventional surgical therapies, endoluminal treatments are distinguished by their "minimally invasive" nature.

Expandable endoluminal devices can be comprised of a graft or a stent component with or without a graft covering over the stent interstices. They can be designed to expand when a restraint is removed or to be balloon-expanded from their delivery diameter, through a range of intermediary diameters, up to a maximal, pre-determined functional diameter.

It remains desirable to provide an improved system and method of deployment of implantable endoluminal devices that facilitates, among other things, ease of deployment and/or controlled deployment and/or positioning of an endoluminal device at the treatment site.

BRIEF DESCRIPTION OF DRAWINGS

The accompanying drawings are included to provide a further understanding of the disclosure and are incorporated in and constitute a part of this specification, illustrate embodiments of the disclosure, and together with the description, serve to explain principles of the disclosure.

DETAILED DESCRIPTION OF THE ILLUSTRATED EMBODIMENTS

Figure 1:
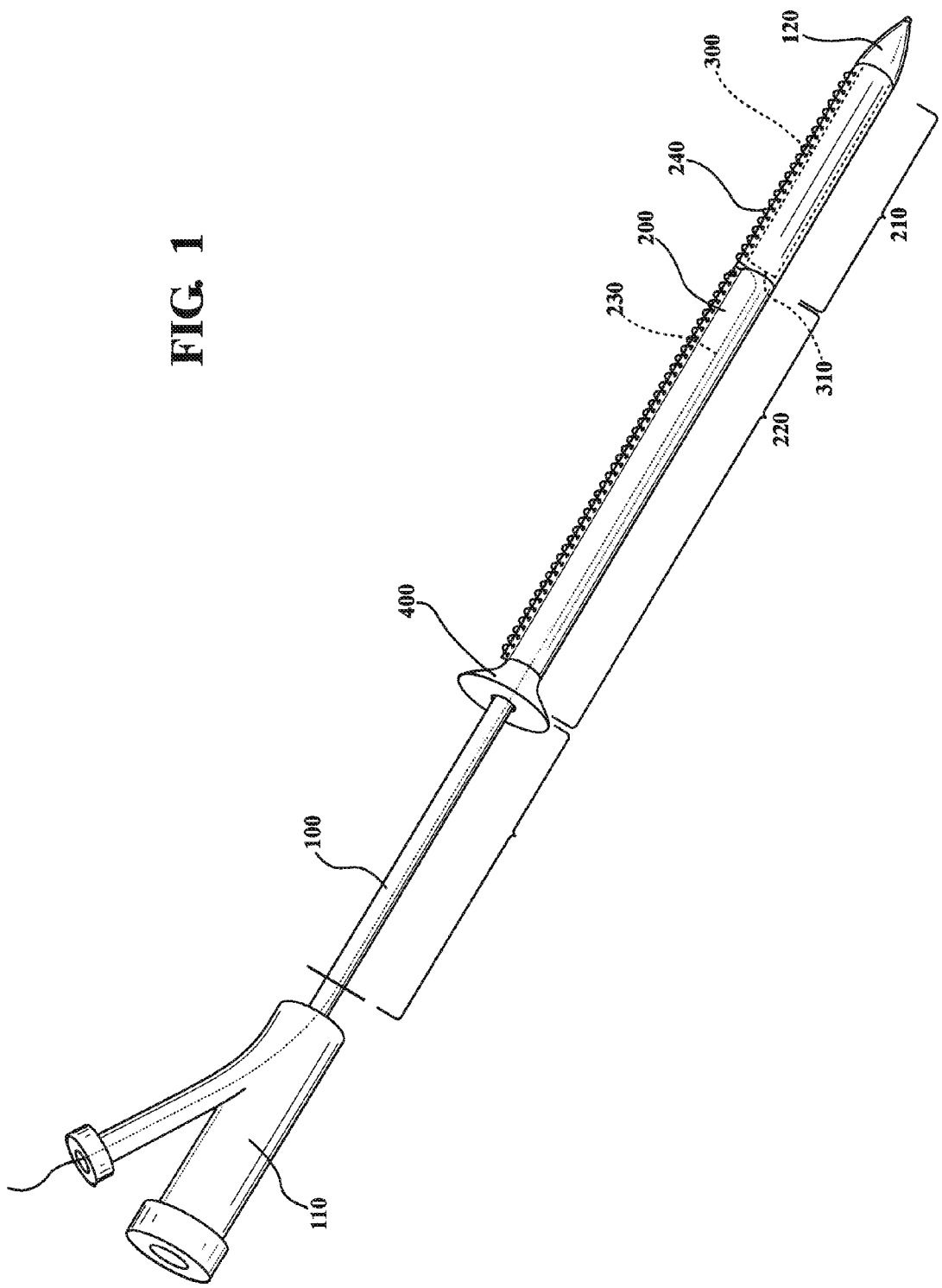
FIG. 1 is a perspective view of a catheter assembly.

Persons skilled in the art will readily appreciate that various aspects of the present disclosure can be realized by any number of methods and apparatuses configured to perform the intended functions. Stated differently, other methods and apparatuses can be incorporated herein to perform the intended functions. It should also be noted that the accompanying drawing figures referred to herein are not all drawn to scale, but can be exaggerated to illustrate various aspects of the present disclosure, and in that regard, the drawing figures should not be construed as limiting. Finally, although the present disclosure can be described in connection with various principles and beliefs, the present disclosure should not be bound by theory.

Throughout this specification and in the claims, the term "distal" refers to a location that is, or a portion of an endoluminal device (such as a stent-graft) that when implanted is, further downstream with respect to blood flow than another portion of the device. Similarly, the term "distally" refers to the direction of blood flow or further downstream in the direction of blood flow.

The term "proximal" refers to a location that is, or a portion of an endoluminal device that when implanted is, further upstream with respect to blood flow than another portion of the device. Similarly, the term "proximally" refers to the direction opposite to the direction of blood flow or upstream from the direction of blood flow.

With further regard to the terms proximal and distal, and because the present disclosure is not limited to peripheral and/or central approaches, this disclosure should not be narrowly construed with respect to these terms. Rather, the devices and methods described herein can be altered and/or adjusted relative to the anatomy of a patient.

Throughout this specification and in the claims, the term "leading" refers to a relative location on a device which is closer to the end of the device that is inserted into and progressed through the vasculature of a patient. The term "trailing" refers to a relative location on a device which is closer to the end of the device that is located outside of the vasculature of a patient.

In various embodiments, a catheter assembly utilizes a constraining sleeve which releasably constrains an expandable implant, such as an expandable endoluminal stent graft, toward a first outer peripheral dimension suitable for endoluminal delivery of the implant toward a treatment site, such as a vascular member in a patient's body. For the purposes of the disclosure, the term "constrain" may mean (i) to limit the expansion, either through self-expansion or assisted by a device, of the diameter of an expandable implant or (ii) to cover or surround but not otherwise restrain an expandable implant (e.g., for storage or biocompatibility reasons and/or to provide protection to the expandable implant and/or the vasculature).

In various embodiments, a distal portion of the sleeve is openable to allow outward expansion of the implant toward a second outer peripheral dimension larger than the first outer peripheral dimension. A proximal portion of the sleeve extends past a proximal end of the implant and toward a proximal end of the catheter to allow access to the proximal portion of the sleeve by a user. After opening the distal portion of the sleeve to allow expansion of the implant, the user can remove the sleeve by pulling the proximal portion of the sleeve. In other embodiments, a handle or knob can be coupled to the proximal portion of the sleeve to facilitate sleeve removal.

Figure 2:
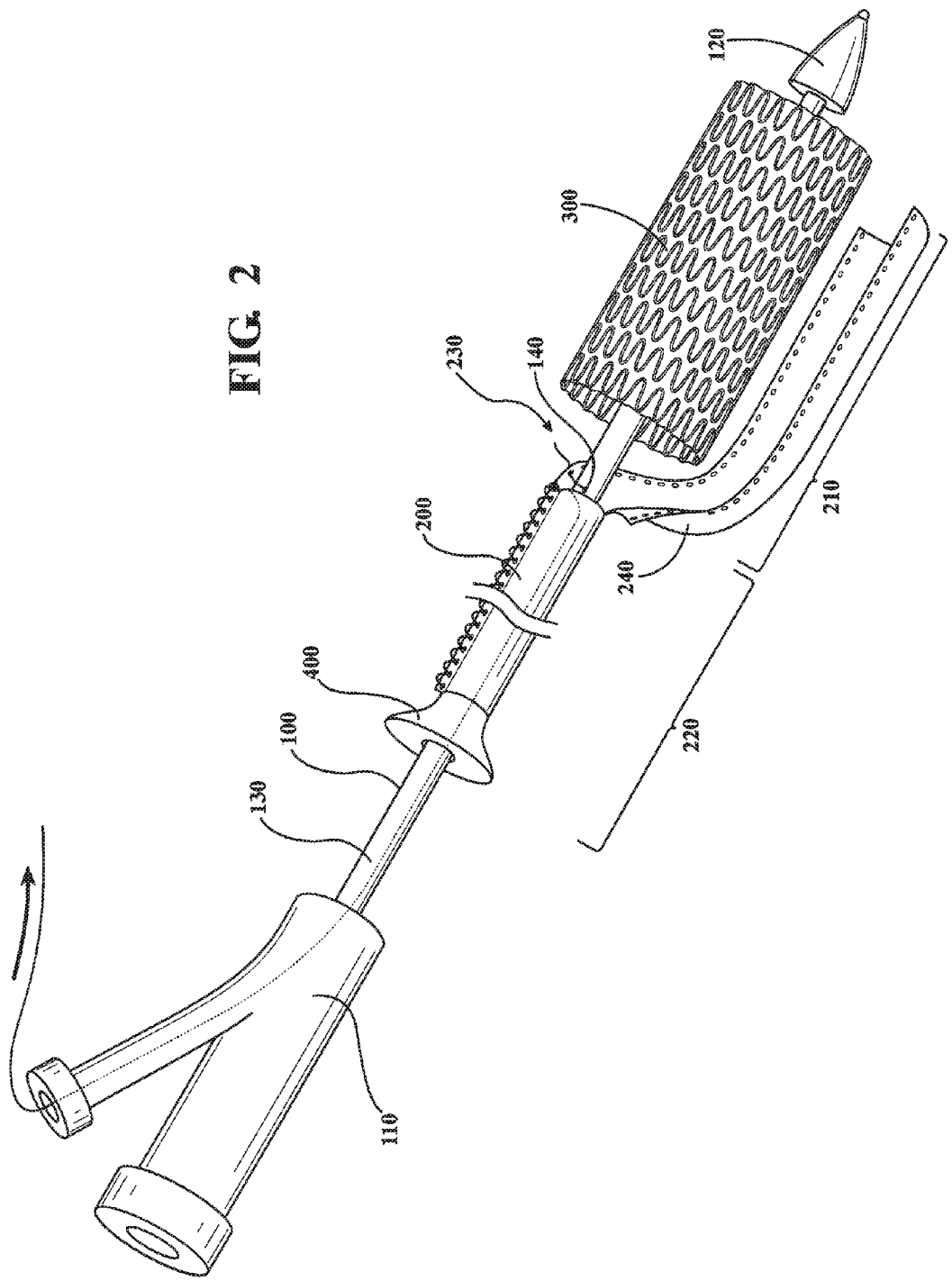
FIG. 2 is a perspective view of a catheter assembly illustrating opening of a primary sleeve.
Figure 3:
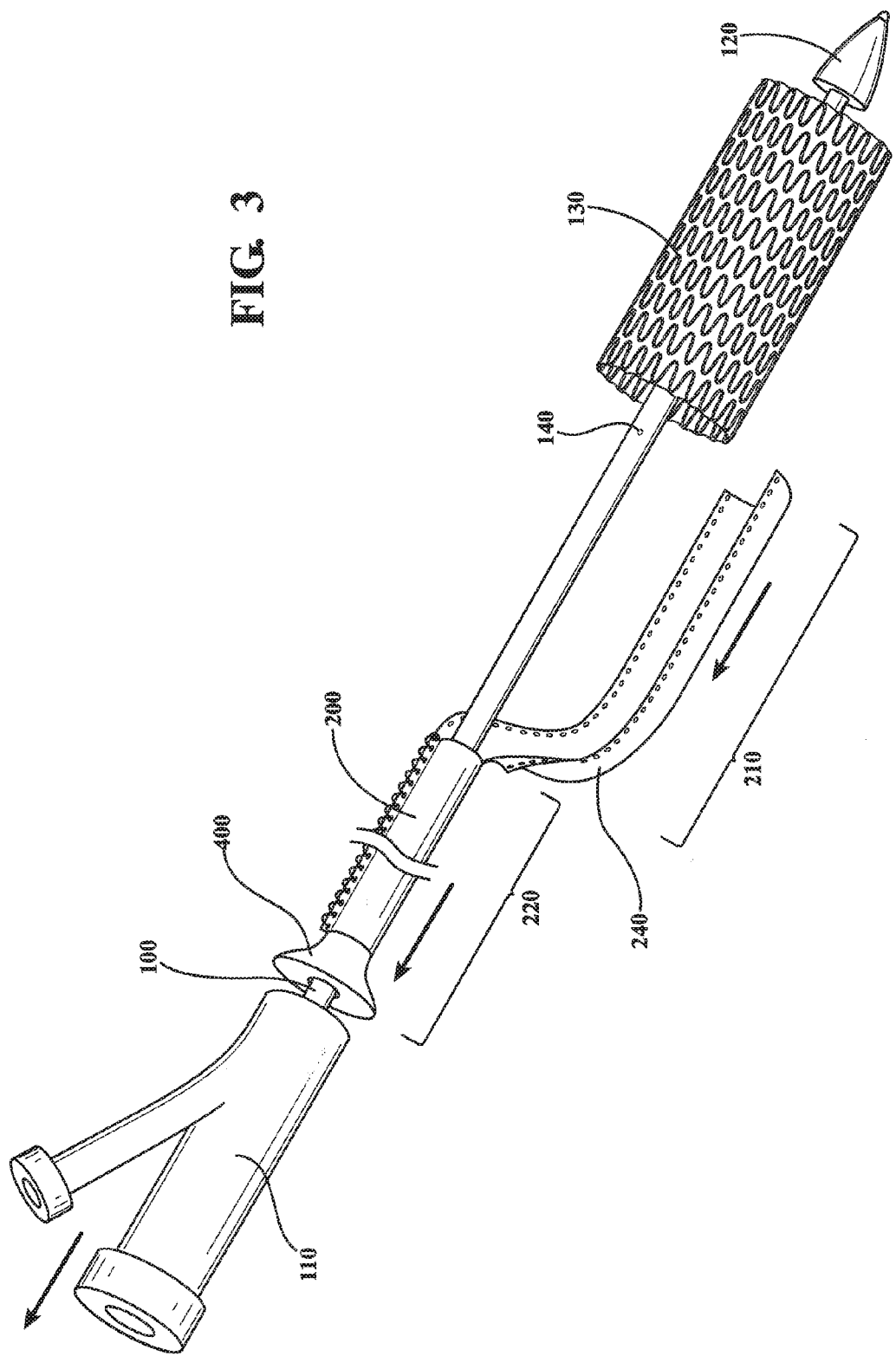
FIG. 3 is a perspective view of a catheter assembly illustrating retraction of primary sleeve.

In various embodiments, for example as illustrated in FIGS. 1-3, a catheter assembly 10 includes a catheter 100 having opposite proximal 110 and distal 120 ends, and a lumen 130 extending between the proximal 110 and distal 120 ends. The catheter assembly 10 also includes an expandable implant 300, such as an expandable endoluminal stent graft, mounted to the distal end 120 of the catheter 100. The implant 300 can be self-expanding, or the implant 300 can be expanded by an expandable device, such as a balloon.

In various embodiments, the catheter assembly 10 includes a constraining sleeve which releasably constrains the implant 300 toward collapsed configuration having a first outer peripheral dimension, for example as illustrated in FIG. 1, suitable for endoluminal delivery of the implant 300 toward a treatment site, such as a vascular member in a patient's body. Constraining sleeves can be tubular and configured to constrain an expandable implant. In such configurations, sleeves can be formed from a thin wall tube of material extending over or a sheet of one or more materials wrapped or folded around the expandable implant. Alternatively, a sheet may be formed by flattening a thin-wall tube. Sleeves can comprise materials similar to those used to form a graft member, such as ePTFE, or other suitable films or membranes.

In various embodiments, sleeves can be formed by wrapping or folding a sheet of material(s), such that two generally parallel edges of the sheet are substantially aligned. Said alignment may or may not be parallel to or coaxial with the catheter shaft of a catheter assembly. In various embodiments, the edges of the sheet of material(s) do not contact each other.

In various embodiments, the edges of the sheet of material(s) do contact each other and are coupled with a coupling member. In various other embodiments, the edges of the sheet of material(s) are aligned so that the edges of the same side of the sheet or sheets (e.g., the front or back of the sheet) are in contact with or at least in proximity to each other. In still other embodiments, the edges of opposite sides of the sheet of material(s) are in contact with each other, such that the edges overlap each other, such that a portion of one side of the sheet is in contact with a portion of the other side. Stated differently, the front of the sheet may overlap the rear of the sheet, or vice versa.

In various embodiments, the sheet of material(s) used to form the sleeve(s) may comprise a series of openings that extend along portions of or the substantial length of each edge. In such configurations, an elongated coupling member can be woven or stitched through the series of openings in the sheet of material(s), thereby releasably securing each of the two edges together and forming a tube.

In various embodiments, the coupling member or a plurality of coupling members can be woven or otherwise configured to release or "open" selective portions of the sleeve or open portions of the sleeve in stages. In FIG. 1-3, for example, a constraining sleeve 200 includes a distal portion 210 that extends generally over the implant 300. A coupling member 230 is woven through openings 240 in the sleeve 200 to secure the edges of sleeve 200 along the distal portion 210 and thereby releasably restrain the implant 300 toward a constrained or first outer peripheral dimension suitable for endoluminal delivery, as shown illustratively in FIG. 1. The distal portion 210 of the sleeve 200 can be released or opened by displacing the coupling member 230 from the openings 240 along the distal portion 210 of the sleeve 200 to allow outward expansion of the implant 300 toward a second outer peripheral dimension larger than the first outer peripheral dimension, as shown illustratively in FIG. 2. The distal portion of the sleeve, for example, can be opened to allow expansion of the implant toward a deployed outer peripheral dimension, which may be generally the same as the vessel to be repaired or slightly larger than the vessel to be treated to provide a traction fit within the vessel.

In various embodiments, for example as illustrated in FIG. 2, the coupling member 230 can be routed through a catheter lumen 130 via a side opening 140 in the catheter 100 to facilitate access and actuation of the coupling member 230 by a user.

The sleeve 200 also includes a proximal portion 220 that extends toward a proximal end 110 of the catheter 100 to facilitate access to or otherwise actuation of the proximal portion 220 of the sleeve 200 by a user. After opening the distal portion 210 of the sleeve 200 to allow expansion of the implant 300, the user can remove the sleeve 200 by accessing and pulling the proximal portion 220 of the sleeve 200, thereby displacing the distal portion 210 of the sleeve 200 away from the implant 300.

In various embodiments, a knob or handle can be interconnected to the proximal portion of the sleeve to facilitate sleeve removal. The handle can be movably coupled or otherwise releasably coupled to the catheter to allow removal of the sleeve by displacement of the handle relative to the catheter. In FIGS. 1-3, for example, a handle 400 can be slidably coupled to the catheter 100 for generally axial movement between a first position, as shown in FIGS. 1 and 2, and a second position, as shown in FIG. 3. Displacement of the handle 400 toward the second position results in displacement of at least the distal portion 210 of the sleeve 200 away from the implant 300.

In other embodiments, a catheter assembly includes a plurality of flexible sleeves that can releasably constrain an expandable implant, such as an expandable endoluminal stent graft, in a dimension suitable for endoluminal delivery of the implant to a treatment site, such as a vascular member in a patient's body; and further can constrain the implant to an intermediate outer peripheral dimension or otherwise a plurality of intermediate outer peripheral dimensions or stages larger than the first outer peripheral dimension but smaller than an unconstrained or second outer peripheral dimension, thereby facilitating selective axial and/or rotational positioning of the implant at the treatment site prior to full deployment and expansion of the implant.

Thus, after opening the distal portion of the sleeve, as described above, or "primary sleeve" in this context, the implant can expand toward and be releasably restrained toward an intermediate outer peripheral dimension by a secondary sleeve (not shown). The secondary sleeve can be held and opened by an elongated member arrangement, as earlier described. The secondary sleeve can also be fixedly secured to and remain with the implant at the treatment site.

It should be readily appreciated that displacement of the primary sleeve away from the implant, as generally described above, while the implant is maintained in the intermediate outer peripheral dimension, removes the primary sleeve as a potential barrier between the implant or portions of the implant, such as anchors or side branch openings, and a target vessel wall at the treatment site.

Although a number of specific configurations of constraining members (for example, primary and secondary members) and sleeves (for example, primary and secondary sleeves) have been discussed, the use of any number and/or configuration of constraining members and any number of sleeves is within the scope of the present disclosure.

Expandable implants, as described herein, may comprise a self-expandable device, such as a self-expandable stent graft. Such devices dilate from a radially collapsed configuration to a radially expanded configuration when unrestrained. Expandable implant may also comprise a device that is expanded with the assistance of a secondary device such as, for example, a balloon. Further, catheter assembly may comprise a plurality of expandable implants. The use of a catheter assembly with any number of expandable implants is within the scope of the present disclosure.

The coupling member, as discussed herein, may comprise a woven fiber. In other embodiments, the coupling member may comprise a monofilament fiber. Any type of string, cord, thread, fiber, or wire which is capable of maintaining a sleeve in a tubular shape is within the scope of the present disclosure.

It will be apparent to those skilled in the art that various modifications and variations can be made in the present disclosure without departing from the spirit or scope of the disclosure. Thus, it is intended that the present disclosure cover the modifications and variations of this disclosure provided they come within the scope of the appended claims and their equivalents.

Likewise, numerous characteristics and advantages have been set forth in the preceding description, including various alternatives together with details of the structure and function of the devices and/or methods. The disclosure is intended as illustrative only and as such is not intended to be exhaustive. It will be evident to those skilled in the art that various modifications may be made, especially in matters of structure, materials, elements, components, shape, size and arrangement of parts including combinations within the principles of the disclosure, to the full extent indicated by the broad, general meaning of the terms in which the appended claims are expressed. To the extent that these various modifications do not depart from the spirit and scope of the appended claims, they are intended to be encompassed therein.

What is claimed is:

1. A catheter assembly comprising:
  a catheter having a leading end, a trailing end and a lumen extending between the leading end and the trailing end;
  an expandable device positioned toward the leading end of the catheter, the expandable device having a collapsed configuration suitable for endoluminal delivery of the expandable device to a vascular treatment site and an expanded configuration having an outer peripheral dimension larger than the outer peripheral dimension of the collapsed configuration;
  a primary sleeve extending around the expandable device, wherein the primary sleeve comprises a sheet of material having first and second major surfaces and a plurality of openings extending between the first major surface and the second major surface, the primary sleeve comprising a thin-wall tube; and
  a primary coupling member engaged with the openings in the primary sleeve for releasably coupling portions of the sheet to one another to constrain the expandable device toward the collapsed configuration,
  wherein the primary sleeve includes a distal portion that extends over the expandable device and is openable by disengaging the primary coupling member from the primary sleeve to allow outward expansion of the expandable device toward the expanded configuration, the primary sleeve being separate from the expandable device and having a proximal portion slidably attached to a portion of the catheter, the proximal portion of the primary sleeve being configured to axially move from a first position to a second position resulting in displacement of the primary sleeve with a portion of the primary coupling member engaged with the proximal portion of the primary sleeve, the portion of the primary sleeve, the portion of the catheter being accessible by a user to facilitate removal of the primary sleeve from the treatment site after expansion of the expandable device toward the expanded configuration.

2. The catheter assembly as set forth in claim 1, wherein the primary coupling member extends through the lumen of the catheter toward a proximal end of the catheter to allow access to the proximal portion of the primary sleeve by a user.

3. The catheter assembly as set forth in claim 2, wherein the primary coupling member extends through a side opening formed in the catheter and into the lumen.

4. The catheter assembly as set forth in 3, further comprising a knob coupled to the proximal portion of the primary sleeve, the knob being slidably attached to the portion of the catheter such that the proximal portion of the primary sleeve is slidably attached to the portion of the catheter via the knob.

5. The catheter assembly as set forth in 4, wherein the knob is releasably coupled to the catheter.

6. The catheter assembly as set forth in 4, wherein the knob is slidably coupled to the catheter for movement between a first position, wherein at least a portion of the sleeve overlaps the expandable device, and a second position, wherein the sleeve is spaced apart from the expandable device.

7. The catheter assembly as set forth in claim 1, wherein the expandable device is a self-expanding stent graft.

8. The catheter assembly as set forth in claim 1, wherein the primary sleeve is formed from ePTFE.

9. The catheter assembly of claim 1, wherein the portion of the catheter includes a shaft portion of the catheter adjacent the trailing end of the catheter.

10. A method of, said method comprising:
  providing the catheter assembly of claim 1;
  endoluminally delivering the leading end of the catheter toward the treatment site;
  allowing expansion of the expandable device by opening the primary sleeve by displacing the primary coupling member from the openings in the primary sleeve; and
  removing the primary sleeve from the treatment site.

11. The method as set forth in claim 10 including displacing the primary coupling member through the lumen of the catheter.

12. The method as set forth in claim 11 including displacing the primary coupling member through a side opening in the catheter.

13. The method as set forth in claim 10 including providing a knob attached to the primary sleeve and slidably coupled to the catheter for movement between a first position, wherein at least a portion of the sleeve overlaps the expandable device, and a second position, wherein the sleeve is spaced apart from the expandable device.

14. The method as set forth in claim 13 including displacing the sleeve away from the expandable device by displacing the knob from the first position toward the second position.

* * * * *